United States Patent [19]

Zoia et al.

[11] Patent Number: 5,053,028

[45] Date of Patent: Oct. 1, 1991

[54] DISPOSABLE DIAPER WITH IMPROVED HOOK AND LOOP FASTENER SYSTEM

[75] Inventors: Anthony J. Zoia, North Oaks; Roland R. Midgley, Minneapolis; Donald L. Plaschko, Woodbury; William L. Melbye, St. Paul; Leigh E. Wood, Woodbury; Susan K. Nestegard, Woodbury; John A. Miller, Woodbury, all of Minn.

[73] Assignee: Minnesota Mining and Manufacturing Company, St. Paul, Minn.

[21] Appl. No.: 419,385

[22] Filed: Oct. 10, 1989

Related U.S. Application Data

[63] Continuation-in-part of Ser. No. 142,552, Jan. 11, 1988, abandoned.

[51] Int. Cl.⁵ .................................. A61F 13/15
[52] U.S. Cl. ................................... 604/385.1
[58] Field of Search ................ 604/385.1, 389, 390, 604/391

[56] References Cited

U.S. PATENT DOCUMENTS

| | | | |
|---|---|---|---|
| 3,359,980 | 12/1967 | Rosenblatt | 128/284 |
| 3,620,217 | 11/1971 | Gellert | 128/284 |
| 3,848,594 | 11/1974 | Buell | 128/284 |
| 3,869,761 | 3/1975 | Schaar | 24/73 |
| 3,931,666 | 1/1976 | Karami | 24/73 |
| 3,989,048 | 11/1976 | Cepuritis et al. | 128/187 |
| 4,047,529 | 9/1977 | Karami | 128/287 |
| 4,074,397 | 2/1978 | Rosin | 24/73 |
| 4,127,132 | 11/1978 | Karami | 128/287 |
| 4,173,042 | 11/1979 | Krzewinski-Morris | 2/197 |
| 4,322,875 | 4/1982 | Brown et al. | 24/204 |
| 4,410,327 | 10/1983 | Baggaley | 604/391 |
| 4,475,912 | 10/1984 | Coates | 604/385 |
| 4,537,591 | 8/1985 | Coates | 604/391 |
| 4,585,450 | 4/1986 | Rosch et al. | 604/390 |
| 4,699,622 | 10/1987 | Toussant et al. | 604/389 |
| 4,869,724 | 9/1989 | Scripps | 604/389 |

Primary Examiner—Randall L. Green
Assistant Examiner—Gina M. Gualtieri
Attorney, Agent, or Firm—Gary L. Griswold; Walter N. Kirn; William L. Huebsch

[57] ABSTRACT

A disposable garment or diaper including a laminate and a hook and loop fastener for fastening together portions of the laminate to secure the diaper to an individual. The fastener includes a loop fastener portion adjacent a first end of the laminate comprising a multiplicity of loops, a pair of flexible elongate polymeric tab assemblies having first end portions attached at opposite sides to the laminate adjacent a second end of the laminate and having distal end portions unattached to the laminate, and hook fastener portions at the distal end portions of the tab assemblies comprising a plurality of projecting hook members adapted to make releasable engagement with the loops. The tab assemblies include a layer of pressure sensitive adhesive on the distal end portions adjacent the hook fastener portion which can, after the diaper has been soiled and removed from the individual, be used for securing the soiled diaper in a rolled or folded condition surrounding the soiled portion of the diaper to facilitate its disposal by engagement of the layer of pressure sensitive adhesive with the laminate.

10 Claims, 4 Drawing Sheets

DISPOSABLE DIAPER WITH IMPROVED HOOK AND LOOP FASTENER SYSTEM

CROSS REFERENCE TO RELATED APPLICATION

This application is a continuation in part of U.S. patent application No. 07/142,552 filed Jan. 11, 1988, now abandoned.

TECHNICAL FIELD

The present invention concerns hook and loop fastener systems that are used on inexpensive or disposable garments such as diapers.

BACKGROUND OF THE INVENTION

Various fasteners have been used on inexpensive or disposable garments such as diapers, including lengths of pressure-sensitive adhesive coated tape, snaps, and hook and loop fasteners.

Of these, lengths of pressure-sensitive adhesive coated tape are presently most widely used as the fasteners for disposable diapers. The lengths of tape both afford fastening the diaper in place on an individual such as a baby, and additionally, after the diaper has been soiled and removed from the individual, provide means for securing the soiled diaper in a rolled or folded condition surrounding the soiled portion of the diaper to facilitate its disposal. The presence of relatively small amounts of contaminants such as talcum powder or baby oil either on the pressure-sensitive adhesive or on the portion of the garment to which the pressure-sensitive adhesive is to be adhered by the user can reduce the reliability of such fasteners, however.

The use of hook and loop fasteners on inexpensive or disposable garments such as diapers substantially overcomes this problem of reduced fastener reliability due to contaminants such as talcum powder or baby oil, however, many hook and loop fasteners are too expensive to be economically used on disposable diapers. Thus, inexpensive portions for hook and loop fasteners are being developed that can securely close the diaper and allow a limited number (e.g., 10) openings and closings of the fastener without seriously degrading it, and are sufficiently inexpensive that they can economically be used on a disposable diaper or similar garment. While such hook and loop fasteners can provide secure fastening to hold the diaper in place and allow opening and closing of the fastener to inspect the condition of the diaper, the location of the hook and loop fastener portions that allows the diaper to be attached to an individual does not typically allow those fastener portions to secure the diaper in a rolled or folded condition surrounding a soiled portion thereof after the diaper is removed from an individual

DISCLOSURE OF THE INVENTION

The present invention provides a hook and loop fastening system for a disposable garment such as a diaper that both affords the advantage of reliability despite contaminants such as talcum powder or baby oil on the diaper, and provide means, after the diaper is soiled and removed, for securing the diaper in a rolled or folded condition surrounding the soiled portion of the diaper to facilitate its disposal.

According to the present invention there is provided a disposable garment or diaper of the type including a generally rectangular laminate and hook and loop fastener means for fastening together portions of the laminate to secure the diaper to an individual, such as a baby. The fastener means includes loop fastener portion means adjacent a first end and including a multiplicity of loops, and a pair of flexible elongate rectangular polymeric tab assemblies having first end portions attached to the laminate adjacent an opposite second end and having distal end portions unattached to the laminate, and hook fastener portion means having a plurality of projecting hook members adapted to make releasable engagement with the loops on the loop fastener means included in the distal end portions of the tab assemblies. The tab assemblies include a layer of pressure-sensitive adhesive which provides, after the diaper has been soiled and removed from the individual, means for securing the soiled diaper in a rolled or folded condition surrounding the soiled portion of the diaper to facilitate its disposal by engagement of the layer of pressure sensitive adhesive with the laminate.

BRIEF DESCRIPTION OF DRAWING

The present invention will be further described with reference to the accompanying drawing wherein like reference numerals refer to like parts in the several views, and wherein.

DESCRIPTION OF THE PREFERRED EMBODIMENTS

Figure 1:
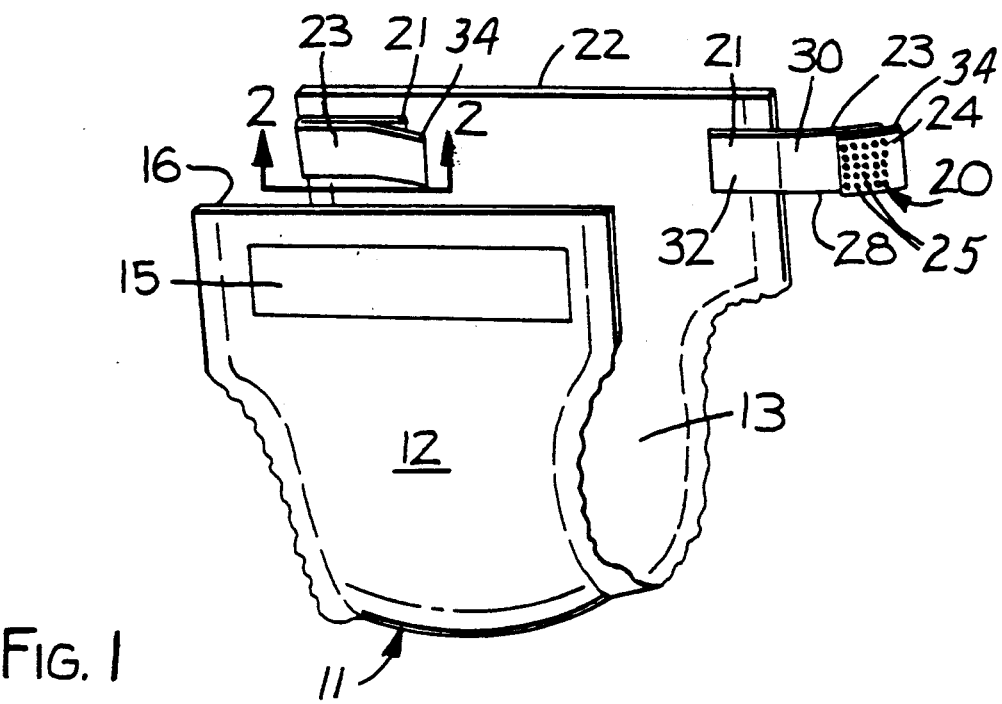
FIG. 1 is a perspective view of a disposable diaper according to the present invention.

Referring now to FIG. 1 there is shown a disposable garment or diaper according to the present invention generally designated by the reference numeral 10.

The diaper 10 is of the type including a generally rectangular laminate 11 including an outer liquid-impermeable polymeric film 12 and an inner absorbing layer 13. The diaper 10 also includes hook and loop fastener means for fastening together portions of the laminate 11 to secure the diaper 10 to an individual, such as a baby. The hook and loop fastening means includes loop fastener portion means, which, as illustrated is an elongate rectangular loop fastener portion 15 having a multiplicity of loops on its outer surface, which loop fastener portion 15 is adhered to the film 12 across what is intended to be the front of the diaper 10 adjacent and along a first end 16 of the rectangular diaper 10. Also included in the hook and loop fastening means are a pair of flexible elongate rectangular polymeric tab assemblies 20 having first end portions 21 attached to the laminate 11 adjacent an opposite second end 22 and having distal end portions 23 unattached to the laminate 11, and hook fastener means or portions 24 having a plurality of hook members 25 that are adapted to make releasable engagement with the loops on the loop fastener portion 15 with each of the hook fastener portions 24 being included in the distal end portion 23 of a different one of the tab assemblies 20. The tab assemblies 20 each include an elongate polymeric strip 28 having a layer 27 of pressure-sensitive adhesive entirely along on surface (i.e., a length of pressure sensitive adhesive coated tape of the type sold as KR-2272 by 3M Company, St. Paul, Minnesota). One end portion of the layer 27 of pressure sensitive adhesive helps attach the first end portion 21 of the tab assembly 20 to the laminate 11 and an opposite end portion adheres a backing 26 of the hook fastener portion 24 from which the hook members 25 project to the distal end portion of the strip 28. A central portion 30 of the layer 27 of pressure sensitive adhesive provides both means to position the tab assembly 20 in a storage position (FIG. 2), and, after the diaper 10 has been soiled and removed from the individual, means for securing the soiled diaper 10 in a rolled or folded condition surrounding the soiled portion of the diaper 10 (not shown) to facilitate its disposal by engagement of the layer 27 of pressure sensitive adhesive with the film 12 or other portions of the laminate 11.

Each of the tab assemblies 20 also includes a release liner 32 having a major portion permanently attached by a layer of adhesive 33 to the nonwoven layer 13 of the laminate 11 opposite the end portion of the strip 28 adhered to the film 12 and having a minor portion extending past the edge of the laminate 11 and adhered to the layer 27 of pressure sensitive adhesive. In a storage positions of the tab assemblies 20 used in shipping the diaper 10 to the user, their distal end portions 23 are folded over to releasably adhere the central portions 30 of the layers 27 of pressure sensitive adhesive on the distal end portions 23 adjacent the hook fastener portion 24 along the release liners 32 (see the left tab assembly 20 in FIG. 1 and FIG. 2) to protect the central portion 30 of the layer of pressure sensitive adhesive 27 and to protect the hook fastener portions 24 from chance unintentional engagement with various substrates prior to application of the diaper 10.

Figure 3:
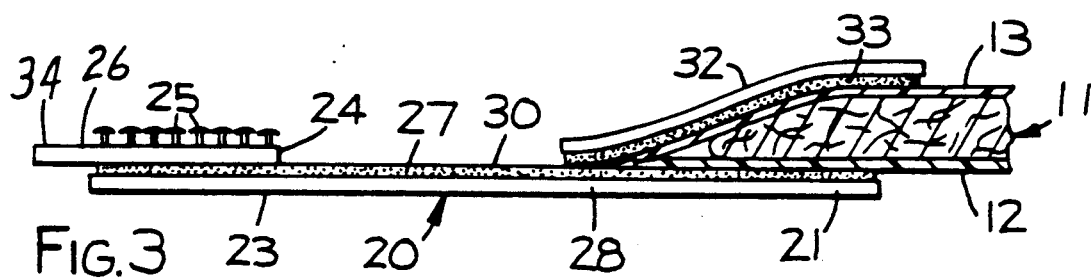
FIG. 3 is is an enlarged fragmentary sectional view similar to FIG. 2 except that the tab assembly is shown in a ready position.

To use the diaper 10, a person may easily peel open the tab assemblies 20 to a ready position shown for the right tab assembly 20 in FIG. 1 and in FIG. 3 to afford releasable engagement of the hook fastener portions 24 with the elongate loop fastener portion 15. Subsequently, as indicated above, after the diaper 10 has been soiled and removed from the individual, the central portion 30 of at least one of the layers 27 of pressure sensitive adhesive provides means for securing the soiled diaper 10 in a rolled or folded condition surrounding the soiled portion of the diaper 10 (not shown) to facilitate its disposal by engagement of at least one of the central portions 30 of the layers 27 of pressure sensitive adhesive with the film 12 of the laminate 11.

The loop fastener portion 15 includes a backing layer which could be a nonwoven material, but is preferably a polymeric film (e.g., polyethylene), and a multiplicity of fibers having portions bonded to the backing along a front surface at spaced bonding locations to form arcuate portions of the fibers projecting from the front surface of the backing between the bonding locations. The arcuate portions have a height from the backing of less than about 0.64 centimeters (0.250 inch) and preferably less than about 0.318 centimeters (0.125 inch). The width of the bonding locations should be between about 0.013 to 0.190 centimeter (0.005 and 0.075 inch), and the width of the arcuate portions of the fibers should be between about 0.152 and 0.889 centimeter (0.06 and 0.35 inch). The fibers in the arcuate portions project to about the same height above the front surface, which height is at least one third, and preferably one half to one and one half the distance between the bonding locations, the individual fibers are less than 15 denier in size, and the fibers collectively have a basis weight in the range of 5 to 200 grams per square meter (and preferably in the range of 10 to 75 grams per square meter) measured along the front surface of the backing to provide sufficient open area between the fibers along the arcuate portions (i.e., between about 10 to 70 percent open area) to afford ready engagement of the fibers along the arcuate portions by the hook members 25 of the hook fastener portion 24. Preferably the sheet material is made from the fibers and backing by forming the fibers into a sheet of fibers having arcuate portions projecting in the same direction from spaced anchor portions of the sheet of fibers, and bonding the spaced anchor portions of the sheet of fibers to the backing so that the arcuate portions project from the front surface of the backing. This forming of the fibers is preferably done by providing first and second generally cylindrical spur gear like corrugating members each including a plurality of uniformly spaced ridges defining its periphery, mounting the corrugating members in axially parallel relationship with portions of the ridges of the corrugating members in mesh with each other, rotating at least one of the corrugating members, feeding the sheet of fibers between the meshed portions of the ridges of the rotating corrugating members to generally conform the sheet of fibers to the periphery of the first corrugating member, thereby forming the arcuate portions of the sheet of fibers in spaces between the ridges of the first corrugating member and the anchor portions of the sheet of fibers along outer surfaces of the ridges of the first corrugating member, and retaining the formed sheet of fibers along the periphery of the first corrugating member after it has moved past the meshing portions of the ridges. The anchor portions of the sheet of fibers are then bonded to the front surface of the backing while they are on the end surfaces of the ridges on the first corrugating member, and the thus formed sheet material is separated from the first corrugating member.

The film backing preferably is in the range of about 0.0025 to 0.013 centimeters (0.001 to 0.005 inch) thick which allows the backing to be printed by conventional methods along one of its surfaces with graphics (such as advertising, instructions or locating marks) which will be visible through the loop portions of the fibers due to their large percentage of open area. The individual fibers may be of many polymeric materials such as polypropylene. When the contacting portions of the backing and the fibers are of the same thermoplastic material, bonding of the fibers to the backing can be done by sonic welding or other means of applying heat and pressure to fuse the fibers to the backing at the bonding dilocation. Alternatively, or when the contacting portions of the backing and the fibers are of different materials, the fibers may be adhesively bonded to the backing such as by softening a thermoplastic adhesive layer of the backing by sonic energy or other means of applying heat and pressure to adhere the fibers to the backing at the bonding locations.

Alternatively, the loop fastener portion 15 can include a backing layer which could be a nonwoven material, but is preferably a polymeric film (e.g., polyethylene), and has a plurality of through stitches formed with polymeric strands by a stitch-knitting machine such as the "Malimo" type Malipol Stitch-Knitting Machine manufactured by Textima in East Germany and distributed in the United States by Chima, Inc. of Reading, Pa., that form the multiplicity of loops 15 along its first surface adapted to be releasably mechanically engaged by the hooks on the mating hook fastener portions 24. Prior to being stitched to form the loops, the film backing layer may be printed with one or more symbols, including written or pictorial instructional material, a brand name, or a pattern or design to improve the aesthetic appeal of the diaper 10 or to serve as indices that aid the user in fitting diapers onto an infant consistently from fitting to fitting. Such printing remains functionally visible through the loops.

The unitary polymeric hook fastener portions 24 each comprise the plate like backing 26 that is thin strong and flexible, and a multiplicity of the resiliently flexible spaced hook members 25 projecting at generally a right angle from the upper surface of a major portion of the backing 26. A minor portion 34 of the the backing 26 projects from one side of the hook members 25 and is positioned to project from the end of the strip 28 to which the backing 26 opposite the hook members 25 is adhered so that the minor portion 34 can be manually grasped to facilitate pealing the tab assembly 20 from its storage position to its ready position, to facilitate engaging the hook members 25 with the loops on the loop fastener portion 15 to attach the diaper 10, and subsequently to peal the hook members 25 from the loop fastener portion 15 to remove the diaper 10 and thereafter adhere the adhesive central portion 30 of the adhesive layer 27 to a portion of the diaper to facilitate its disposal. The hook members 25 each comprise a stem portion attached at one end to the backing 26, and a head portion at the end of the stem portion opposite the backing 26. The head portion projects past the stem portion on at least one of two opposite sides, and has a rounded surface opposite the stem portion to help the head portion enter between loops in the loop fastener portion 15. The hook members 25 are more easily and firmly engaged with many types of loop fastener portions than the hook members on known commercially available hook fastener portions, in large part because their head portions are very small in cross section compared to head portions on the hook members of those commercially available hook fastener portions, and thus more easily penetrate into a loop fastener portion. Specifically, the hook members 25 each have a height dimension from the upper surface of the backing 26 of less than 1.5 millimeter (0.06 inch) and preferably of about 0.10 centimeter (0.04 inch). The stem and head portions each have generally the same thickness dimension of less than 0.046 centimeter (0.018 inch) and preferably in the range of 0.020 to 0.028 centimeter (0.008 to 0.012 inch) in a first direction parallel to the surfaces of the backing 26. The stem portions each have a width dimension in the range of 0.018 to 0.03 centimeter (0.007 to 0.012 inch) in a second direction generally at a right angle to the first direction and parallel to the surfaces of the backing 26 (which second direction is aligned with the length of the strip), and the head portions each have a width dimension in the second direction that is between 0.007 and 0.038 centimeter (0.003 and 0.015 inch) greater than the width dimension of the stem portion, less than 0.1 centimeter, and preferably in the range of 0.04 to 0.065 centimeter (0.016 to 0.026 inch). Hook members 25 of this small size have been found to easily penetrate between and engage the loops on loop fastener portions, but individually have little holding power so that the hook fastener portion 24 includes at least 45, and preferably 70 to 100 per square centimeter (at least 300 and preferably 450 to 645 hook members 25 per square inch) of the spaced hook members 25 projecting from the upper surface of the backing 26 to provide the required holding power, while the total cross sectional area occupied by the head portions in a plane parallel to the upper surface is less that 32 percent and preferably in the range of 5 to 15 percent of the area of the upper surface to retain the ease of engagement of the large number of projecting hook members 25 with the loop fastener portion 15.

Preferably the hook fastener portion 24 is made of a polypropylene/polyethylene copolymer or a blend of polypropylene with an ethylene-vinyl acetate b ock copolymer or a styrene-ethylene-butylene-styrene block copolymer, and has an elastic modulus within the range from 100 to 500 megaPascals as measured in said second direction (i.e., the direction the parts of the head portion project over the stem portion) according to ASTM D 882.80a, which measurement generally comprises measuring the initial slope of the stress strain curve from a tensile test of the material. Hook members 25 with an elastic modulus in that range exhibit an excellent ability to initially engage the loop fastener portion 15, and to resist shear and peel forces tending to separate them from the loop fastener portion 15 once they are engaged. This combination of properties is believed to be due to the ability of the hook members 25 to resiliently bend to move between loops during engagement, and to resiliently bend when they are pulled out of engagement with the loops which resilient bending minimizes breaking of both the small hook members 25 and the loops, and thus prolongs the useful life and esthetics of both the hook fastener portion and the loop fastener portion with which it is mated.

Hook fastener portions having the number of hook portions per unit area of the size and made of the polymeric material indicated above have found to have a very smooth and non abrasive feel when the hook portions are pressed against a persons skin, which is desirable so that the hook portions will not cause discomfort or injury to the skin of a person with which inadvertent contact with the hook portions is made.

The hook fastener portions 24 are made by an adaptation of a known method of making hook fastener portions described in U.S. Pat. Nos. 3,226,113; 3,557,413; 4,001,366; 4,056,593; and 4,189,098, which method generally includes extruding a thermoplastic resin through a die shaped to form a backing 26 layer and spaced ridges projecting above an upper surface of the backing 26 layer that have the cross sectional shape of the hook members 25 to be formed, transversely cutting the ridges at spaced locations along their length to form discrete portions of the ridges, and stretching the backing 26 layer to separate those portions of the ridges which are then the spaced hook members 25.

Figure 4:
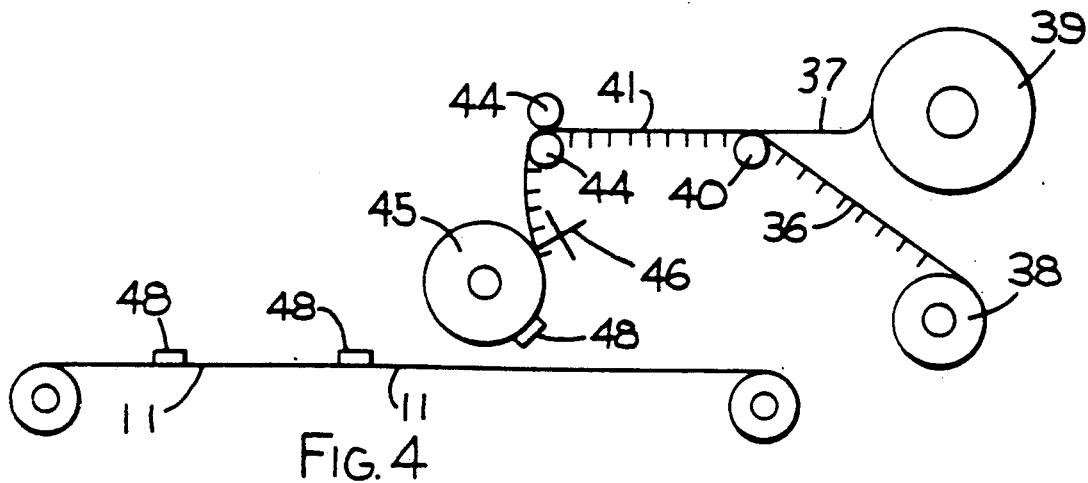
FIG. 4 is a schematic view illustrating a method of applying the tab assembly shown in FIGS. 1 through 3.

FIG. 4 schematically illustrates attaching a layered structure 48 including one of the the hook fastener portions 24, and the strip 28 and the layer 27 of pressure sensitive adhesive in the form of a length of tape to a concatenation of laminates 11 to be formed into diapers 10 moving along a production line. A strip 36 of hook material made by the method described above from which the hook fastener portion 24 can be cut and pressure sensitive adhesive coated tape 37 from rolls 38 and 39 respectively are joined at a roller 40 with the hook material 36 along one edge of the tape 37, whereupon the composite 41 thus formed is guided and fed by nip rollers 44 onto the periphery of a vacuum wheel 45 having a greater peripheral speed than the speed the composite 41 is fed by the nipping rollers 44. The end of the composite 41 slips on the periphery of the vacuum wheel 45 until a timed cutter 46 cuts an end portion therefrom which forms the layered structure 48 and is then carried into engagement with one of the laminates 11 moving past the vacuum wheel 45.

Figure 5:
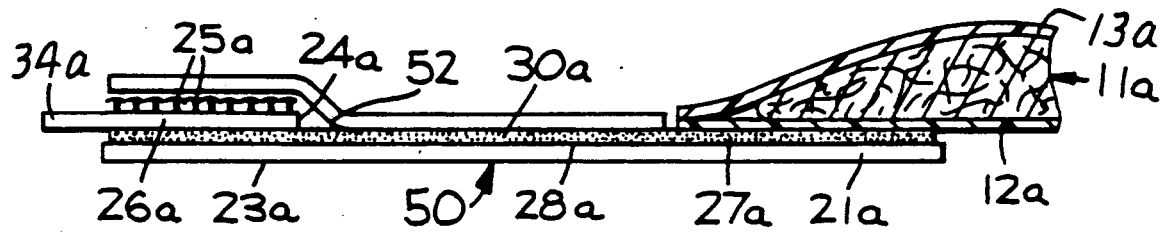
FIG. 5 is an enlarged sectional view which shows detail of a first alternate embodiment of a tab assembly that can be incorporated in the diaper of FIG. 1 and includes hook fastener portion means and a layer of pressure sensitive adhesive used in disposing of the diaper, which tab assembly is shown in a stored position.

FIG. 5 illustrates an alternate embodiment of a tab assembly 50 that can be used on the diaper 10 of FIG. 1, which embodiment has essentially the same parts as the the tab assembly 20 which are identified using the same reference numerals to which has been added the suffix "a". The tab assembly 50 differs from the tab assembly 20 in that the release liner 32 and adhesive layer 33 are not used and the central portion 30a of its layer 27a of pressure sensitive adhesive is protected by a removable release liner 52 which may, as illustrated, extend both over the central portion 30a of the pressure sensitive adhesive 27a and over the hook members 25a of the hook fastener portion 24a to provide a storage position of the tab assembly 50 at which the central portion 30a of the adhesive 27a and the hook fastener portion 24a are protected from chance unintentional engagement with various substrates prior to application of the diaper 10 to an individual. To use the diaper 10a, a person may fold back the end portion of the release liner 32 extending over the hook members 25a so that the tab assembly 50 is in a ready position (not shown) at which the hook members 25a may be engaged with parts of the loop fastener portion. Subsequently, after the diaper 10a has been soiled and removed from the individual, the release liner 52 may be pealed away from the central portion 30a of the layer 27a of pressure sensitive adhesive to provide means for securing the soiled diaper 10a in a rolled or folded condition surrounding the soiled portion of the diaper 10a (not shown) to facilitate its disposal by engagement of the central portion 30a of the layer 27a of pressure sensitive adhesive with the laminate 11a. Alternately (not shown) the release liner 52 could extend over only the central portion 30a of the layer 27a of pressure sensitive adhesive and not over the fastener portion 24a so that the tab assembly 50 is ready for use to engage the loop fastener portion without folding back the end portion of the release liner 52. Also, the end of the release liner 52 adjacent the laminate 11a could be permanently adhered or attached to the strip 28a and/or to the laminate 11a so that the release liner 52 would not be separated from the tab assembly 50 when it is pealed from the layer 27a of pressure sensitive adhesive.

Figure 6:
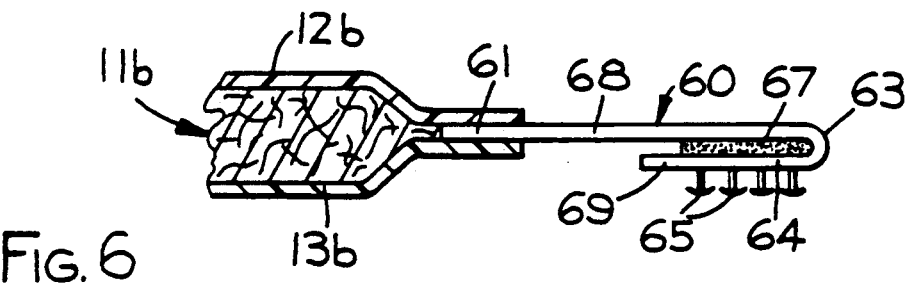
FIG. 6 is an enlarged sectional view which shows detail of a second alternate embodiment of a tab assembly that can be incorporated in the diaper of FIG. 1 and includes hook fastener portion means and a layer of pressure sensitive adhesive used in disposing of the diaper, which tab assembly is shown in a ready position.
Figure 7:
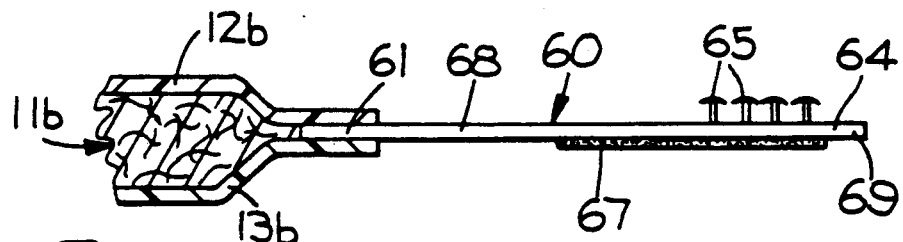
FIG. 7 is an enlarged sectional view similar to FIG. 6 but shown with the tab assembly in a dispose position.
Figure 8:
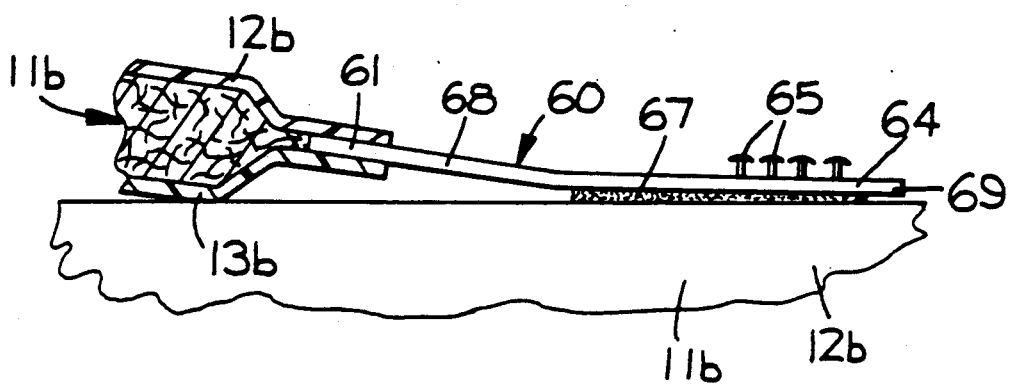
FIG. 8 is an enlarged fragmentary view similar to FIG. 7 except that the tab assembly is shown attached by the layer of pressure sensitive adhesive to a surface of the diaper to facilitate disposal of the diaper.

FIGS. 6 through 8 illustrate a second alternate embodiment of a tab assembly 60 that could be used on a diaper 10b similar to the diaper 10 illustrated in FIG. 1 for which diaper 10b similar parts have been identified with the same reference numerals to which the suffix "b" has been added. Like the tab assembly 20, the tab assembly 60 has a first end portion 61 attached to the laminate 11b and has a distal end portion 63 unattached to the laminate 11b, and hook fastener means or portions 64 comprising a plurality of projecting hook members 65 included in the distal end portion 63 that are adapted to make releasable engagement with the loops on a loop fastener portion. The tab assembly 60 includes an elongate polymeric strip 68 having an end portion bonded (e.g., by adhesive, heat bonding, or sonic sealing) between the film 12b and nonwoven layer 13b of the laminate 11b, and a layer 67 of pressure-sensitive adhesive adjacent the projecting hook members on the distal end portion 63 which could be placed there by coating or applying a piece of transfer adhesive. An end part 69 of the portion of the polymeric strip 68 defining the distal end portion 63 and including the hook fastener portion 64 is folded over and releasably adhered in that position by the layer 67 of pressure sensitive adhesive. The hook fastener portion 64 is engagable with the loop fastener portion to attach the diaper to an individual with the end part 69 folded over in a ready position as shown in FIG. 6. After the diaper is subsequently removed, the end part 69 can be pealed to a dispose position generally in alignment with the rest of the strip 68 as is shown in FIG. 7. The layer 67 of pressure-sensitive adhesive can be provided with lower internal cohesive strength than the strength of it adhesion to the strip along both of its sides so that upon such pealing of the end part 69 the layer 67 of adhesive will split with a portion remaining adhered to both portions of the layer 67 to which it was originally adhered, so that as illustrated in FIGS. 7 and 8 it will have a large surface area for engagement with the film 12b or other portions of the laminate 11b as is shown in FIG. 8 to secure soiled and removed diaper 10b in a rolled or folded condition surrounding the soiled portion of the diaper 10b.

A preferred pressure sensitive adhesive suitable for the layer 67 of adhesive that has less internal or cohesive strength than adhesive strength to polypropylene of which the polymeric strip 68 can be made and which has good adhesion to polyethylene of which the film 12b is typically made is a mixture by weight of 65 percent of a styrene/isoprene block copolymer (e.g., Kraton 1107 commercially available from Shell Chemical Company, Houston, Tex.), 30 percent of an aliphatic-/aromatic liquid hydrocarbon tackifying resin (e.g., Escorez 2520 commercially available from Exxon Chemical Company, Houston, Tex.), and 5 percent of a hydrogenated hydrocarbon solid tackifying resin (e.g., Escorez 5300 commerically available from Exxon Chemical Company).

Alternatively, though not shown, the surface portions of the strip 68 to which the opposite sides of the layer 67 of pressure sensitive adhesive are adhered in the ready position (FIG. 6) could be treated by known processes and/or release coatings so that the layer 67 of adhesive would remain adhered only to the end part 69 or only to the portion of the strip adjacent the end part 69 after the end part 69 is pealed to the dispose position generally in alignment with the rest of the strip 68.

The hook members 65 of the hook fastener means or portion 64 are illustrated as being integral with the strip 68, which could be achieved by making the strip and hook members 65 as a unit by the extrusion method described above. Alternatively, hook portions with mushroom shaped heads could be embedded in the strip 68 using the method described in U.S. Pat. No. 4,290,832, incorporated herein by reference, or separate hook fastener portions of the type described with reference to FIGS. 1 through 3 could be adhered to the end of the strip 68.

Figure 10:
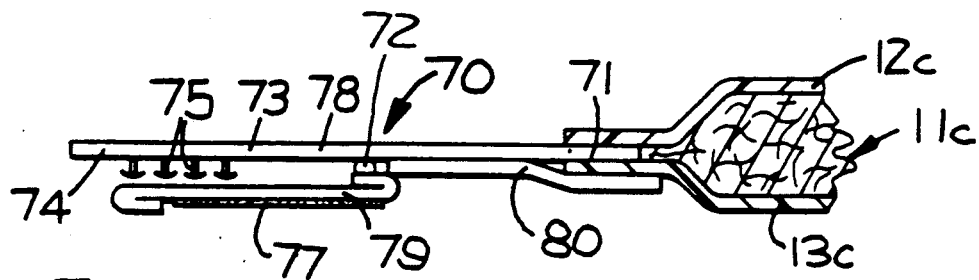
FIG. 10 is an enlarged sectional view similar to FIG. 9 but shown with he tab assembly in a dispose position.
Figure 9:
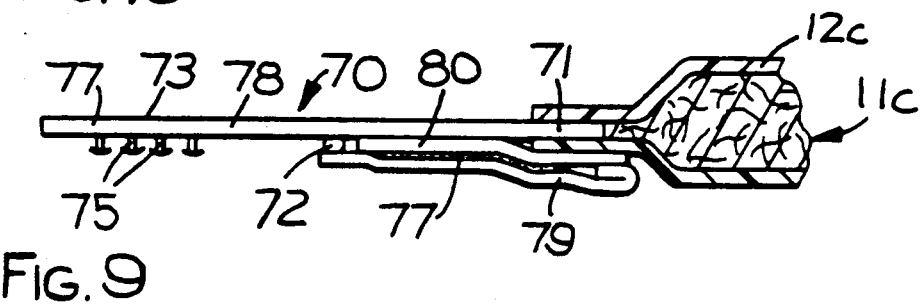
FIG. 9 is an enlarged sectional view which shows detail of a third alternate embodiment of a tab assembly that can be incorporated in the diaper of FIG. 1 and includes a hook fastener portion and layer of pressure sensitive adhesive used in disposing of the diaper, which tab assembly is shown in a ready position.

FIGS. 9 and 10 illustrate a third alternate embodiment of a tab assembly 70 that could be used on a diaper 10c similar to the diaper 10 illustrated in FIG. 1 for which diaper 10c similar parts have been identified with the same reference numerals to which the suffix "c" has been added. Like the tab assembly 20, the tab assembly 70 has a first end portion 71 attached to the laminate 11c and has a distal end portion 73 unattached to the laminate 11c, and a hook fastener means or portion 74 comprising a plurality of projecting hook members 75 along and included in its distal end portion 73 that are adapted to make releasable engagement with the loops on a loop fastener portion. The tab assembly 70 includes an elongate polymeric strip 78 having an end portion bonded (e.g., by adhesive, heat bonding, or sonic sealing) between the film 12c and nonwoven layer 13c of the laminate 11c, and a layer 77 of pressure-sensitive adhesive adjacent the projecting hook members 75 on the distal end portion 73. The layer 77 of pressure sensitive adhesive is coated on a backing 79 permanently attached at one end as by sonic welding or a stripe 72 of permanent adhesive to the strip 78 and is releasably adhered in a ready position of the tab assembly 70 (shown in FIG. 9) to a release liner 80 permanently adhered along portions of the strip 78 and nonwoven layer 13c, at which ready position the hook members 75 could be engaged with a loop fastener portion to attach the diaper 10c to an individual. The backing 79 and attached layer 77 of pressure sensitive adhesive can be manually pealed away from the release liner 80 and folded back to position the layer 77 of pressure sensitive adhesive on the backing over the hook members 75 in a dispose position as shown in FIG. 10 to afford securing the diaper 10c, when soiled and removed, in a rolled or folded condition surrounding the soiled portion of the diaper 10c to facilitate its disposal by engagement of the layer 77 of pressure sensitive adhesive on the backing 79 with the film 12c or other portions of the laminate 11c (not shown).

Alternatively, though not shown, the layer of pressure sensitive adhesive could be preferentially adhered to a backing in the position of the release liner 80, and a release liner could be used in the position of the backing 79 and releasably adhered over the layer of adhesive in the ready position of the tab assembly, which release liner would be pealed from over the layer of adhesive for the dispose position of the tab assembly.

Figure 2:
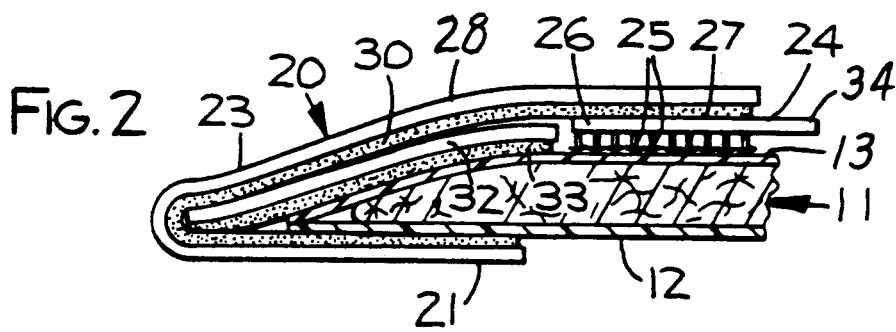
FIG. 2 is an enlarged fragmentary sectional view taken approximately along line 2—2 of FIG. 1 which shows detail of a tab assembly incorporated in the diaper of FIG. 1 that includes hook fastener portion means and a layer of pressure sensitive adhesive used in disposing of the diaper, which tab assembly is shown in a stored position.

As with the hook members 65, the hook members 75 of the hook fastener means or portion 74 are illustrated as being integral with the strip 78, however separate hook fastener portions of the type described with reference to FIGS. 1 through 3 could be adhered to the end of the strip 78.

Figure 11:
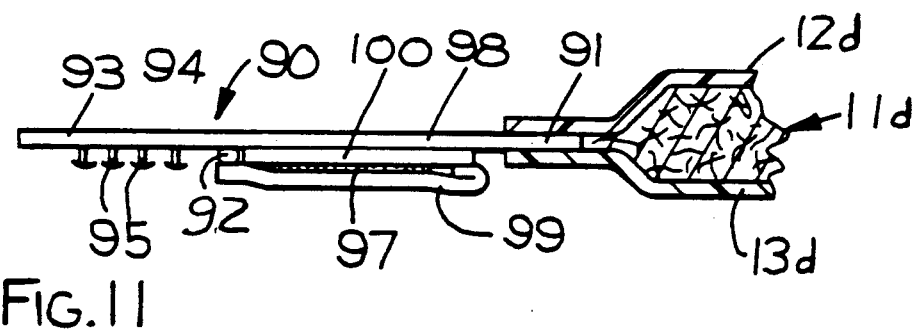
FIG. 11 is an enlarged sectional view which shows detail of a fourth alternate embodiment of a tab assembly that can be incorporated in the diaper of FIG. 1 and includes a hook fastener portion and layer of pressure sensitive adhesive used in disposing of the diaper, which tab assembly is shown in a ready position.
Figure 12:
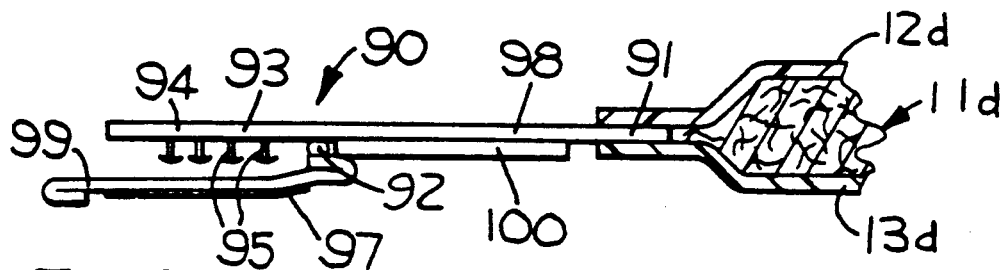
FIG. 12 is an enlarged sectional view similar to FIG. 11 but shown with the tab assembly in a dispose position.

FIGS. 11 and 12 illustrate a fourth alternate embodiment of a tab assembly 90 that could be used on a diaper 10d similar to the diaper 10 illustrated in FIG. 1 for which diaper 10d similar parts have been identified with the same reference numerals to which the suffix "d" has been added. Like the tab assembly 20, the tab assembly 90 has a first end portion 91 attached to the laminate 11c and has a distal end portion 93 unattached to the laminate 11c, and a hook fastener means or portion 94 comprising a plurality of projecting hook members 95 along and included in its distal end portion 93 that are adapted to make releasable engagement with the loops on a loop fastener portion. The tab assembly 90 includes an elongate polymeric strip 98 having an end portion bonded between the film 12d and nonwoven layer 13d of the laminate 11d and a layer 97 of pressure-sensitive adhesive adjacent the projecting hook members on the distal end portion 93. The layer 97 of pressure sensitive adhesive is coated on a backing 99 (i.e., the backing 99 and the layer 97 of pressure sensitive adhesive are a piece of pressure sensitive adhesive coated tape) attached at one end as by sonic welding or a stripe 92 of permanent adhesive to the strip 98 and releasably adhered in a ready position of the tab assembly 90 (shown in FIG. 11) to a release liner 100 adhered along a central portion of the strip 98, at which ready position the hook members 95 could be engaged with a loop fastener portion to attach the diaper 10d to an individual. The backing 99 and attached layer 97 of pressure sensitive adhesive can be pealed away from the release liner 100 and folded back to position the layer of pressure sensitive adhesive over the hook members 95 in a dispose position of the tab assembly 70 as shown in FIG. 12 to afford securing the diaper 10d when soiled and 15 removed, in a rolled or folded condition surrounding the soiled portion of the diaper 10d to facilitate its disposal by engagement of the layer 97 of pressure sensitive adhesive on the backing 99 with the film 12d or other portions of the laminate 11d (not shown).

Alternatively, though not shown, the release liner 100 could be deleted, and the layer 97 of pressure sensitive adhesive could be releasably adhered to the surface of the strip 98, which would then have to have an appropriate surface treatment or release coating. Also alternatively and not shown the layer of pressure sensitive adhesive could be preferentially adhered to a backing in the position of the release liner 100 or to the strip 98, and a release liner could be used in the position of the backing 99 and releasably adhered over the layer of adhesive in the ready position of the tab assembly, which release liner would be pealed from over the layer of adhesive for the dispose position of the tab assembly.

Figure 13:
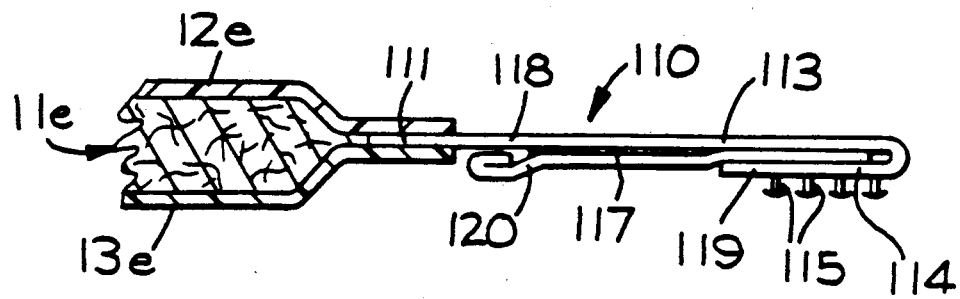
FIG. 13 is an enlarged sectional view which shows detail of a fifth alternate embodiment of a tab assembly that can be incorporated in the diaper of FIG. 1 and includes a hook fastener portion and layer of pressure sensitive adhesive used in disposing of the diaper, which tab assembly is shown in a ready position.

FIG. 13 illustrates yet a fifth alternate embodiment of a tab assembly 110 that could be used on a diaper 10e similar to the diaper 10 illustrated in FIG. 1 for which diaper 10e similar parts have been identified with the same reference numerals to which the suffix "e" has been added. Like the tab assembly 20, the tab assembly 110 has a first end portion 111 attached to the laminate 11e and has a distal end portion 113 unattached to the laminate 11e, and a hook fastener means or portion 114 comprising a plurality of projecting hook members 115 along and included in its distal end portion 113 that are adapted to make releasable engagement with the loops on a loop fastener portion. The tab assembly 110 includes an elonqate polymeric strip 118 having an end portion bonded between the film 12e and nonwoven layer 13e of the laminate 11e and a layer 117 of pressure-sensitive adhesive coated on or adhered to the strip 118 adjacent the projecting hook members on the distal end portion 113. An end part 119 of the portion of the polymeric strip 118 defining the distal end portion 113 and carrying the hook fastener portion 114 is folded over and fixed to an end portion of a release liner 120 releasably adhered over the layer 117 of pressure sensitive adhesive. The hook fastener portion 113 is engagable with the loop fastener portion with the end part 119 folded over in a ready position as shown in FIG. 13, and the portion of the release liner 120 adhered to the layer 117 of pressure sensitive adhesive is separable from the layer 117 of pressure sensitive adhesive to expose it in a dispose position of the tab assembly 110 (not shown) to afford securing the diaper 10e, when soiled and removed, in a rolled or folded condition surrounding the soiled portion of the diaper 10e to facilitate its disposal by engagement of the layer 117 of pressure sensitive adhesive with the film 12e or other portion of the laminate 11e (not shown).

Alternatively, though not shown, the layer of pressure sensitive adhesive could be preferentially adhered to a backing in the position of the release liner 120, and the layer of pressure sensitive adhesive could be releasably adhered to the strip 118 so that the layer of pressure sensitive adhesive would be carried with the backing to a position facing away from and extending over the hook members 115 for the dispose position of the tab assembly.

Figure 14:
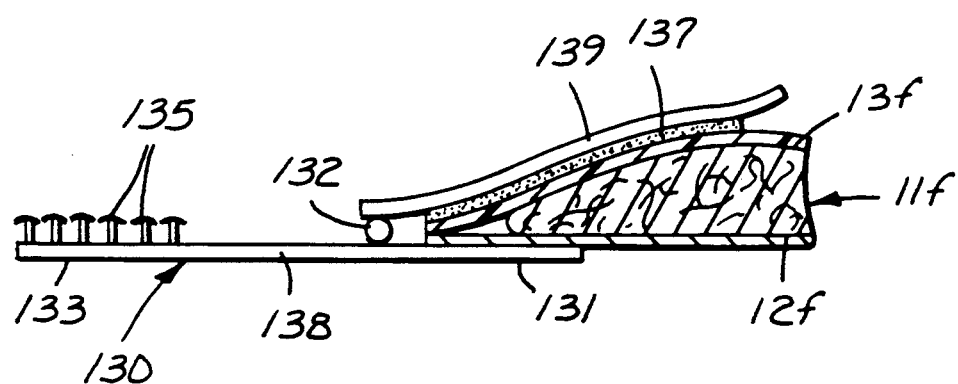
FIG. 14 is an enlarged sectional view which shows detail of a sixth alternate embodiment of a tab assembly that can be incorporated in the diaper of FIG. 1 and includes a hook fastener portion and layer of pressure sensitive adhesive used in disposing of the diaper, which tab assembly is shown in a ready position.
Figure 15:
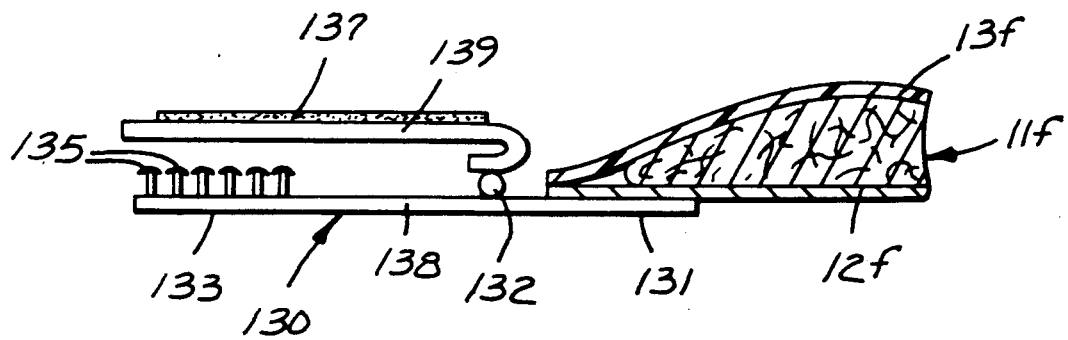
FIG. 15 is an enlarged sectional view similar to FIG. 14 but shown with the tab assembly in a dispose position.

FIGS. 14 and 15 illustrate a sixth alternate embodiment of a tab assembly 130 that could be used on a diaper 10f similar to the diaper 10 illustrated in FIG. 1 for which diaper 10f similar parts have been identified with the same reference numerals to which the suffix "f" has been added. Like the tab assembly 20, the tab assembly 130 has a first end portion 131 attached to the laminate 11f and has a distal end portion 133 unattached to the laminate 11f, and a hook fastener means or portion comprising a plurality of projecting hook members 135 along and included in its distal end portion 133 that are adapted to make releasable engagement with the loops on a loop fastener portion. The tab assembly 130 includes an elongate polymeric strip 138 having an end portion bonded (e.g., by adhesive, heat bonding, or sonic sealing) to the side of the film 12f opposite the nonwoven layer 13f of the laminate 11f. A layer 137 of pressure-sensitive adhesive is coated on a backing 139 permanently attached at one end as by sonic welding or a stripe 132 of permanent adhesive to the strip 138 and is releasably adhered in a ready position of the tab assembly 130 (shown in FIG. 14) along the inner absorbing layer 13f, at which ready position the hook members 135 could be engaged with a loop fastener portion to attach the diaper 10c to an individual. The backing 139 and attached layer 137 of pressure sensitive adhesive can be manually pealed away from the inner absorbing layer 13 and folded back to position the layer 137 of pressure sensitive adhesive on the backing 139 adjacent or over the hook members 135 in a dispose position as shown in FIG. 15 to afford securing the diaper 10f, when soiled and removed, in a rolled or folded condition surrounding the soiled portion of the diaper 10f to facilitate its disposal by engagement of the layer 137 of pressure sensitive adhesive on the backing 139 with the film 12c or other portions of the laminate 11c (not shown).

As with the hook members 65, the hook members 135 of the hook fastener means or portion 134 are illustrated as being integral with the strip 138, however separate hook fastener portions of the type described with reference to FIGS. 1 through 3 could be adhered or otherwise attached to the end of the strip 138.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

We claim:

1. A disposable diaper including
a laminate having first and second opposite major surfaces, first and second opposite ends and opposite sides extending between said opposite ends, and hook and loop fastener means for fastening together portions of said laminate to secure said diaper to an individual, said fastener means including a loop fastener portion fixed on one of said surfaces adjacent the first end of said laminate, said loop fastener portion having an outer surface opposite said laminate and comprising a multiplicity of loops along said outer surface, a pair of flexible elongate tab assemblies each having a first end portion attached to said laminate along a different one of said opposite sides adjacent the second end of said laminate, a distal end portion unattached to said laminate, and a hook fastener portion included in the distal end portion of said tab assembly, said hook fastener portion comprising a plurality of projecting hook members adapted to make releasable engagement with said loops, at least one of said tab assemblies including a layer of pressure sensitive adhesive providing, after the diaper has been soiled and removed from the individual, means for securing the soiled diaper in a rolled or folded condition surrounding the soiled portion of the diaper to facilitate its disposal by engagement of the layer of pressure sensitive adhesive with said laminate.

2. A disposable diaper according to claim 1, wherein each of said tab assemblies includes a layer of pressure sensitive adhesive, said tab assemblies each comprise an elongate polymeric strip having one end portion attached to said laminate and an opposite end portion providing said distal end portion unattached to said laminate, said layer of pressure sensitive adhesive extends entirely along said distal end portion, and said hook fastener portion for each of said tab assemblies comprises a base having upper and lower major surfaces with said plurality of hook members projecting from the upper surface of said base, said lower major surface of the base being attached to said strip along said distal end portion by said layer of pressure sensitive adhesive.

3. A disposable diaper according to claim 1 wherein each of said tab assemblies includes a layer of pressure sensitive adhesive, said tab assemblies each comprise an elongate polymeric strip having one end portion attached to said laminate and an opposite end portion providing said distal end portion unattached to said laminate, said layer of pressure sensitive adhesive extends along said opposite end portion of said polymeric strip, and said tab assemblies each include a release liner adhered along the side of the layer of pressure-sensitive adhesive opposite the polymeric strip.

4. A disposable diaper according to claim 3, wherein said release liner for each of said tab assemblies is attached to one of the surfaces of said laminate, and said distal end portion for each of said tab assemblies is folded so that said release liner is releasably adhered along the layer of pressure sensitive adhesive on said distal end portion.

5. A disposable diaper according to claim 1 wherein each of said tab assemblies includes a layer of pressure sensitive adhesive, said tab assemblies each comprise an elongate polymeric strip having one end portion attached to said laminate and an opposite end portion providing said distal end portion unattached to said laminate, said layer of pressure sensitive adhesive extends along said distal end portion, and said hook members are integrally formed with said strip to provide said hook fastener portion.

6. A disposable diaper according to claim 1 wherein each of said tab assemblies includes a layer of pressure sensitive adhesive, said tab assemblies each comprise an elongate polymeric strip having one end portion attached to said laminate and an opposite end portion providing said distal end portion unattached to said laminate with said layer of pressure sensitive adhesive having one surface adhered to a first part of said strip adjacent said hook fastener portion and an end part of the portion of said polymeric strip defining said distal end portion and carrying said hook fastener portion for each of said tab assemblies being folded over and adhered to the surface of said layer of pressure sensitive adhesive opposite said first part, said hook fastener portion being engageable with said loop fastener portion with said end part folded over, and said end part being movable to a position generally in alignment with said first part to expose said layer of pressure sensitive adhesive to afford securing the diaper, when soiled and removed, in a rolled or folded condition surrounding the soiled portion of the diaper to facilitate its disposal by engagement of the layer of pressure sensitive adhesive with said laminate.

7. A disposable diaper according to claim 6 wherein said layer of pressure sensitive adhesive has greater adhesive strength to said strip than internal cohesive strength so that said layer of adhesive will split with a portion remaining adhered to said end part and a portion remaining adhered to said first part when said end part of said polymeric strip is moved to said position generally in alignment with said first part of said polymeric strip.

8. A disposable diaper according to claim 7 wherein said layer of pressure sensitive adhesive is a mixture by weight of 65 percent of a styrene/isoprene block copolymer, 30 percent of an aliphatic/aromatic liquid hydrocarbon tackifying resin, and 5 percent of a hydrogenated hydrocarbon solid tackifying resin.

9. A disposable diaper according to claim 1 wherein each of said tab assemblies includes a layer of pressure sensitive adhesive, said tab assemblies each comprise an elongate polymeric strip having one end portion attached to said laminate and an opposite end portion providing said distal end portion unattached to said laminate, and a backing having first and second ends and a major surface with said layer of pressure sensitive adhesive along said major surface, said first end of said backing being attached to said distal end portion adjacent said hook fastener portion, and said layer of pressure sensitive adhesive being releasably adhered to one surface of said distal end portion and being separable from said distal end so that said backing can be folded back over said hook fastener portion to expose said layer of pressure sensitive adhesive and afford securing the diaper, when soiled and removed, in a rolled or folded condition surrounding the soiled portion of the diaper to facilitate its disposal by engagement of the layer of pressure sensitive adhesive with said laminate.

10. A disposable diaper according to claim 1 wherein each of said tab assemblies includes a layer of pressure sensitive adhesive, an elongate polymeric strip having one end portion attached to said laminate and an opposite end portion included in said distal end portion unattached to said laminate, and a backing having first and second ends and a major surface with said layer of pressure sensitive adhesive along said major surface, said first end of said backing being attached to said distal end portion adjacent said laminate, and said layer of pressure sensitive adhesive being releasably adhered to one surface of said laminate and being removable from said laminate so that said backing can be folded back to expose said layer of pressure sensitive adhesive and afford securing the diaper, when soiled and removed, in a rolled or folded condition surrounding the soiled portion of the diaper to facilitate its disposal by engagement of the layer of pressure sensitive adhesive with said laminate.

* * * * *